(12) United States Patent
Kurk et al.

(10) Patent No.: US 6,953,332 B1
(45) Date of Patent: Oct. 11, 2005

(54) MANDREL FOR USE IN FORMING VALVED PROSTHESES HAVING POLYMER LEAFLETS BY DIP COATING

(75) Inventors: James L. Kurk, Lino Lakes, MN (US); Chad Q. Cai, Woodbury, MN (US); Steven D. Kruse, Bloomington, MN (US); Yi-Ren Woo, Alcove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/724,007

(22) Filed: Nov. 28, 2000

(51) Int. Cl.⁷ .......................... B29C 33/42; B29C 41/14
(52) U.S. Cl. .................. 425/275; 249/52; 264/302; 264/303; 264/305; 264/DIG. 60
(58) Field of Search ................ 264/302, 303, 264/305, 299, DIG. 60; 425/269, 270, 275; 249/52

(56) References Cited

U.S. PATENT DOCUMENTS

| | | | |
|---|---|---|---|
| 3,717,883 A | 2/1973 | Mosher | |
| 4,135,867 A * | 1/1979 | Stockum | 425/275 |
| 4,222,126 A | 9/1980 | Boretos et al. | |
| 4,265,694 A | 5/1981 | Boretos et al. | 156/242 |
| 4,364,127 A | 12/1982 | Pierce et al. | 3/1.5 |
| 4,417,360 A | 11/1983 | Moasser | |
| 4,556,996 A | 12/1985 | Wallace | |
| 4,731,074 A | 3/1988 | Rousseau et al. | |
| 4,778,461 A | 10/1988 | Pietsch et al. | 623/2 |
| 4,888,009 A | 12/1989 | Lederman et al. | 623/2 |
| 5,116,564 A | 5/1992 | Jansen et al. | 264/255 |
| 5,139,515 A | 8/1992 | Robicsek | |
| 5,376,113 A | 12/1994 | Jansen et al. | 623/2 |
| 5,562,729 A | 10/1996 | Purdy et al. | 623/2 |
| 5,728,340 A * | 3/1998 | Dreibelbis et al. | 264/126 |
| 6,139,575 A | 10/2000 | Shu et al. | |
| 6,171,335 B1 | 1/2001 | Wheatley et al. | |
| 6,174,331 B1 | 1/2001 | Moe et al. | |

FOREIGN PATENT DOCUMENTS

| | | |
|---|---|---|
| EP | 0 331 345 A2 | 9/1989 |
| EP | 0 850 607 A1 | 9/1989 |
| EP | 0 632 711 B1 | 12/1997 |
| NL | 1008349 C | 8/1999 |
| RU | SU 316446 | 10/1971 |
| RU | SU 1144216 | 10/1987 |
| WO | WO9832400 | 7/1998 |
| WO | WO 01/05334 A1 | 1/2001 |

* cited by examiner

Primary Examiner—Stefan Staicovici
(74) Attorney, Agent, or Firm—Westman, Champlin and Kelly, P.A.

(57) ABSTRACT

Improved dip coating methods and mandrels for forming polymer leaflets and valve prostheses generally involve one or more features on the mandrel that facilitate the processing. The mandrel has a top surface and an outer surface comprising a plurality of ridges and contoured surfaces extending to the ridges. An edge on the mandrel separates the top surface and the contoured surfaces, with the mandrel edge corresponding to the free edge of the leaflet. In preferred embodiments, the edge separating the top surface from the contoured surfaces is sharp. The polymer formed on the top surface can be efficiently separated from the remaining portions of the polymer structure to form the free edges of the leaflets.

32 Claims, 9 Drawing Sheets

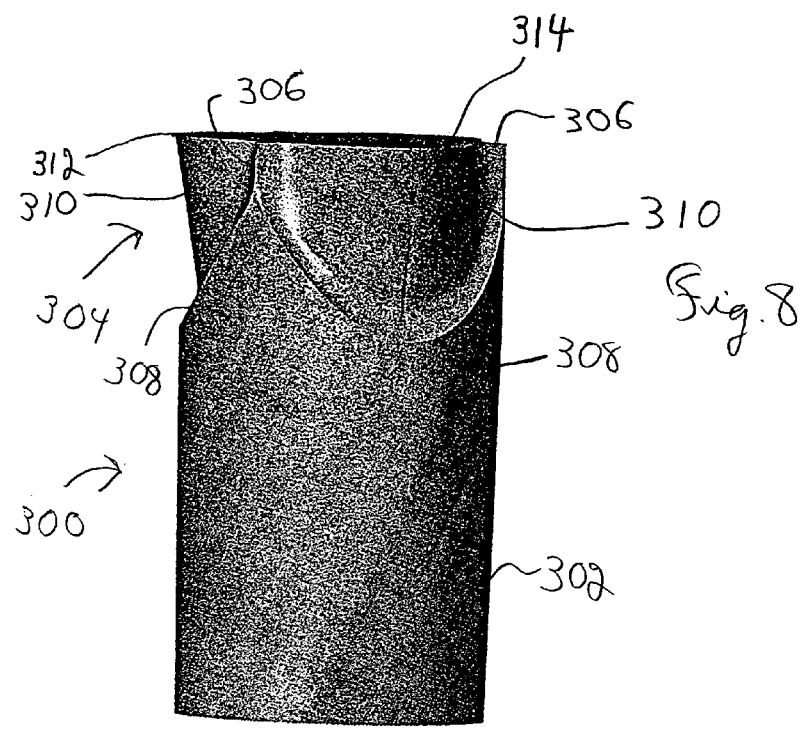
Fig. 8
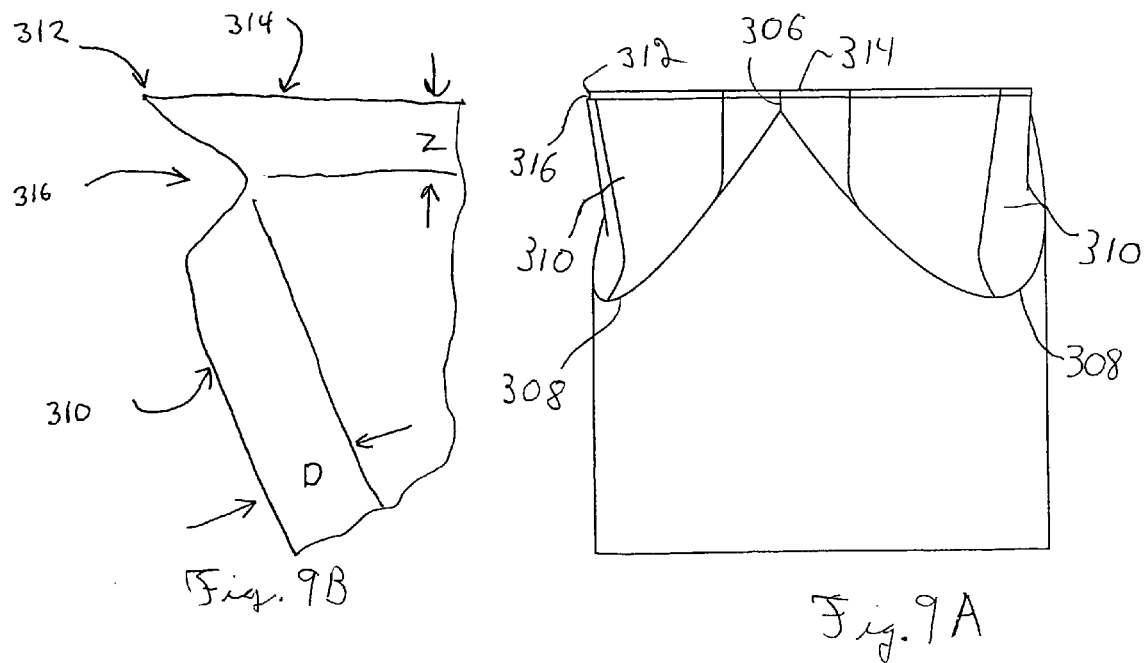
Fig. 9B
Fig. 9A

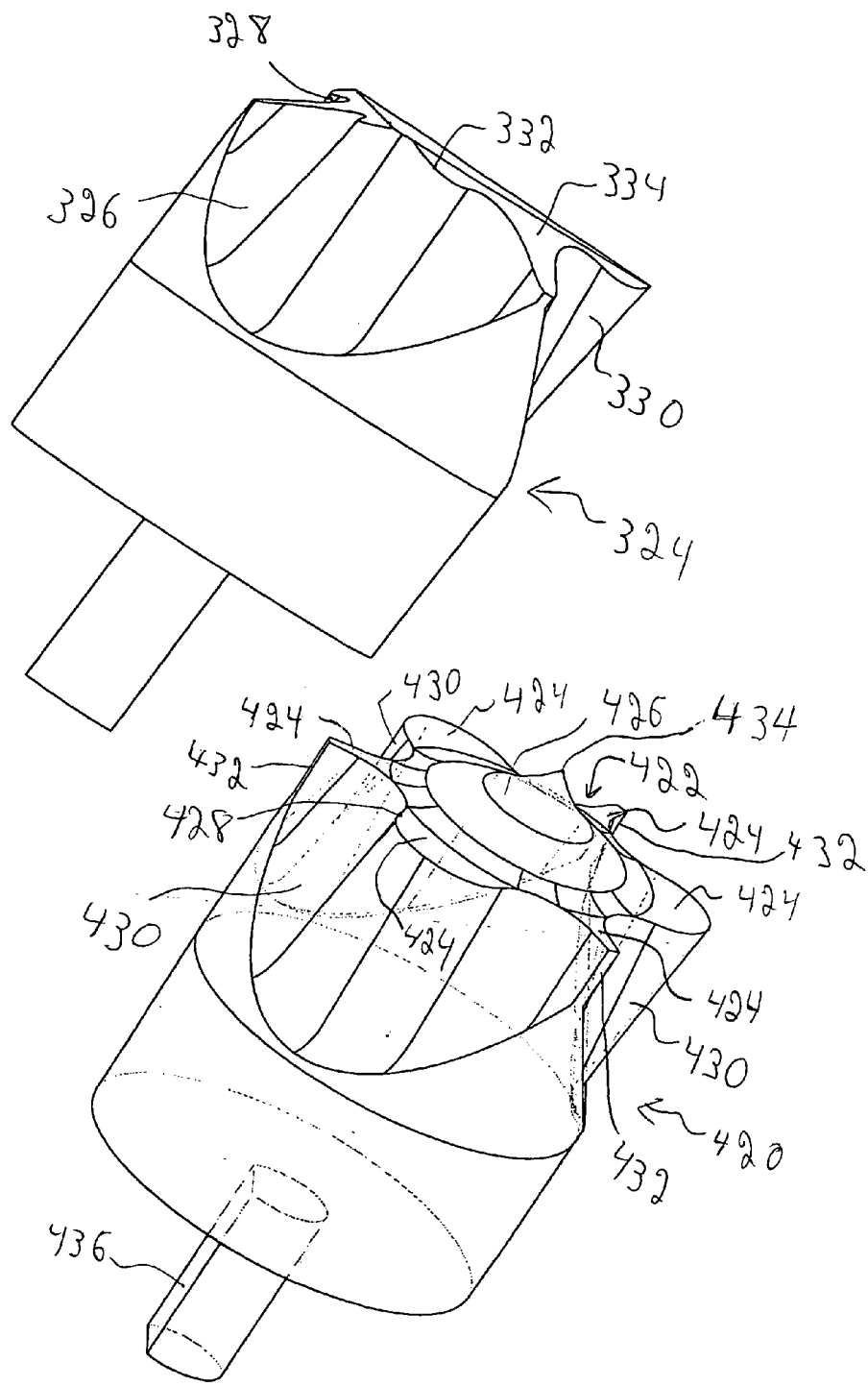

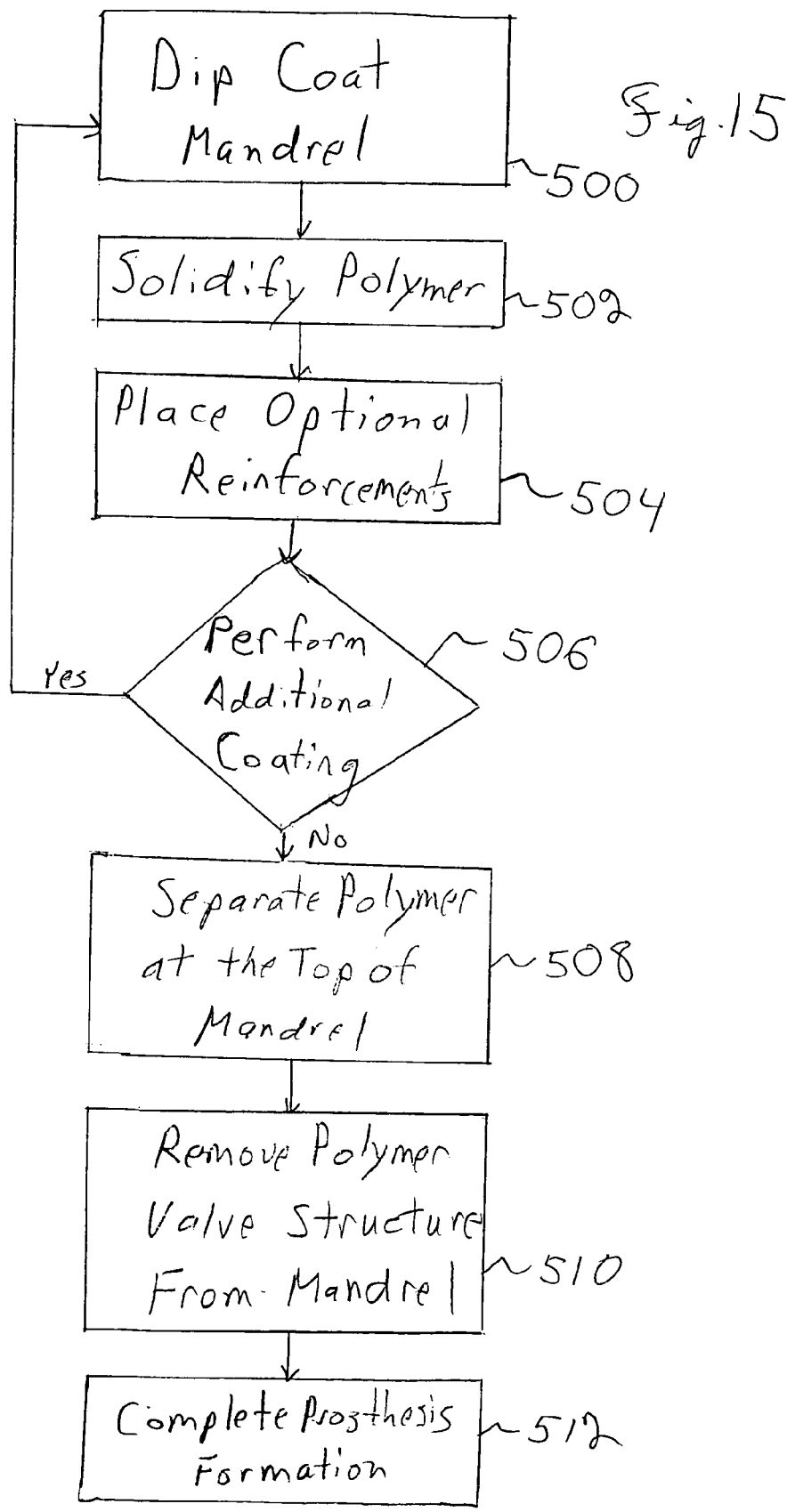

MANDREL FOR USE IN FORMING VALVED PROSTHESES HAVING POLYMER LEAFLETS BY DIP COATING

BACKGROUND OF THE INVENTION

The invention relates to methods for forming valved prostheses with polymer leaflets by dip coating a mandrel. The invention further relates to improved mandrel structures and to improved valved prostheses made by the processes using the improved mandrel structures.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a prosthetic heart valve.

Heart valve insufficiency can be a debilitating and possibly life threatening condition. For example, heart valve regurgitation, i.e., backward leakage of blood at a heart valve, results in reduced pumping efficiency. In addition, pumping inefficiency and pooling of blood in extremities can result from insufficiency of valves in veins.

Some cases of heart valve insufficiency can be repaired by modifications of the original valve in a procedure generally referred to as valvuloplasty. For example, one repair technique uses an annuloplasty ring to provide structural support to the natural annulus of the native valve. For severe cases of heart valve damage, however, reconstructive valvular surgery may not be possible. In such cases, valve replacement may be indicated.

Prosthetic heart valve leaflets or occluders perform the function of opening and closing to regulate the blood flow through the heart valve. Typically, heart valve leaflets must either pivot or flex with each cycle of the heart to open and close. Heart valves function as check valves, which open for flow in one direction and close in response to pressure differentials.

Prostheses can be constructed from natural materials such as tissue, synthetic materials or a combination thereof. Prostheses formed from purely synthetic materials can be manufactured, for example, from biocompatible metals, ceramics, carbon materials, such as graphite, polymers, such as polyester, and combinations thereof. Heart valve prostheses with purely synthetic materials can be manufactured with rigid occluders or leaflets that pivot to open and close the valve, or flexible leaflets that flex to open and close the valve.

Although mechanical heart valves with rigid pivoting occluders have the advantage of proven durability through decades of use, they are associated with blood clotting on or around the prosthetic valve and thromboembolism. Blood clotting can lead to acute or subacute closure of the valve or associated blood vessel. For this reason, patients with mechanical heart valves remain on anticoagulants for as long as the valve remains implanted. Anticoagulants have associated risks and cannot be taken safely by certain individuals.

Heart valve prostheses with flexible leaflets can be constructed with tissue leaflets or polymer leaflets. In prostheses with flexible leaflets, the leaflets are generally designed to approximate natural leaflet function. While the leaflets are flexible, they must have a well defined and stable configuration to properly open and close the valve at each cycle in response to pressure differentials. Also, the leaflets should be durable to provide stable performance over many years of use.

Unlike mechanical valves, tissue based bioprostheses do not require the long term use of anticoagulants due to a lower incidence of thromboembolism. While tissue leaflets have desired flexibility and acceptable hemodynamic performance, tissue leaflets can calcify after implantation, which results in loss of flexibility resulting in improper closure and/or opening of the valve.

Valve prostheses with polymer leaflets have the potential to overcome the shortcomings of both tissue and mechanical valve designs. The polymers incorporated into heart valve prostheses should provide long term stable function to be suitable alternatives for tissue leaflets or pivoting mechanical leaflets.

SUMMARY OF THE INVENTION

In a first aspect, the invention pertains to a mandrel comprising a top surface, and an outer surface comprising a plurality of ridges and contoured surfaces extending between the ridges corresponding to polymer leaflets. In preferred embodiments, an edge on the mandrel separates the top surface and the contoured surfaces, with the mandrel edge corresponding to the free edge of the leaflets.

In a further aspect, the invention pertains to a method for producing polymer leaflets for a polymer valve prosthesis, the method comprising forming a polymer structure by dip coating a mandrel into a polymer liquid. The mandrel preferably has a top surface and an outer surface comprising a plurality of ridges and contoured surfaces extending to the ridges. An edge on the mandrel separates the top surface and the contoured surface with the mandrel edge corresponding to the free edge of the leaflets.

In another aspect, the invention pertains to a mandrel comprising an outer surface having a plurality of ridges and contoured surfaces extending between the ridges. The contoured surfaces correspond to polymer leaflets in a closed configuration. The contoured surfaces corresponding to the leaflets meet contoured surfaces of adjacent leaflets at a sharp edge.

BRIEF DESCRIPTION OF THE DRAWINGS

FIG. 8 is a side perspective view of a mandrel of the invention.

FIG. 9A is a side view of a mandrel with a groove near the edge along the top surface of the mandrel.

FIG. 9B is a fragmentary, expanded view of a corner of the mandrel of FIG. 9A.

FIG. 10 is a side view of a mandrel with leaflet contours having an edge at the top of the mandrel not in a plane.

FIG. 13 is a perspective view of a mandrel with a complex top surface.

FIG. 15 is a flow diagram outlining the dip coating process.

DETAILED DESCRIPTION OF THE ILLUSTRATIVE EMBODIMENTS

Figure 1:
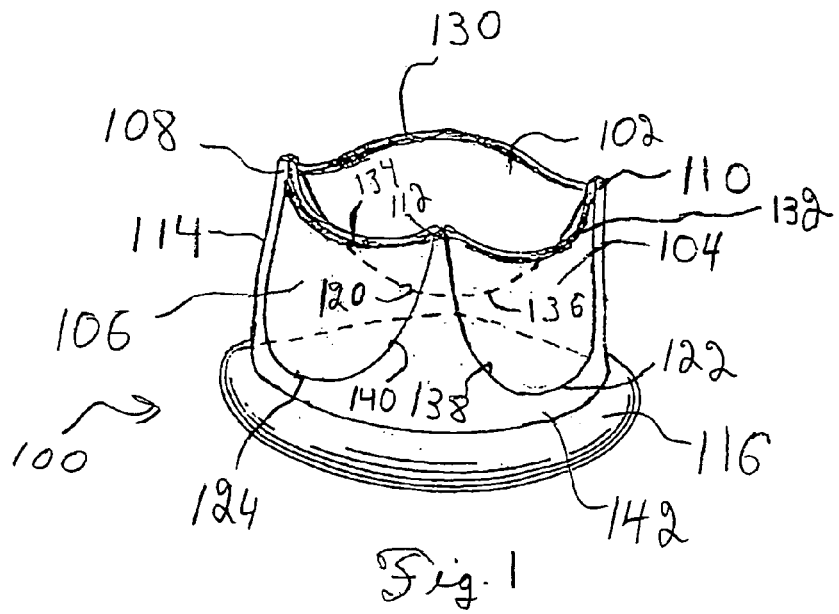
FIG. 1 is a perspective view of a heart valve prosthesis with reinforced polymer leaflets, wherein the valve is in an open configuration.

A dip coating process using an improved mandrel design has been developed to facilitate the production of polymer leaflets for heart valve prostheses. The improved process involves simplified processing to generate the free edge of the leaflets. The edge of the top surface of the mandrel corresponds to the free edge of the leaflets. Thus, the free edge of the leaflets can be formed by removing the polymer that coats the top of the mandrel. In addition, more uniform leaflets can be formed than can be produced using conventional processes which require a more complex finishing process to form the free edge of the leaflet.

The improved polymer leaflets can be used to form valves prostheses, especially heart valve prostheses. Damaged or diseased natural heart valves can be replaced with valved prostheses to restore valve function. Heart valve prostheses of interest have leaflets formed from polymers. The polymers form flexible leaflets similar to native tissue leaflets. The polymer heart valve prosthesis can be designed as a replacement for any heart valve, i.e., an aortic valve, a mitral valve, a tricuspid valve, or a pulmonary valve. In addition, the improved polymer valve prostheses can be used for the replacement of vascular valves. The patient can be an animal, especially a mammal, and preferably is a human.

In a polymer valve, the leaflets are supported by a support structure that includes commissure supports and scallops between the commissure supports. The support structure of the valve may include a sewing cuff or the like for attachment of the valve to the patient's annulus or to the other components of another device.

In some embodiments, the support structure includes a rigid component that maintains the leaflet function of the valve against the forces opening and closing the valve. Valves with a rigid support structure are termed stented valves, and the rigid support is called a stent. The stent provides a scaffolding for the leaflets. The stent includes commissure supports that support the ends of the free edge of the leaflets. Scallops, which support the attached edges of the leaflets, extend between the commissure supports. The stent generally is sufficiently rigid such that only the base of the stent is attached to the patient or other device. As a particular example, heart valve stents are used to support leaflet components within a prosthetic heart valve.

In alternative embodiments, the support structure is not sufficiently rigid to maintain the leaflet function of the valve against the forces opening and closing the valve. In these embodiments, the valve is termed stentless. In a stentless valve, the support structure has commissure supports and scallops to which the leaflets attach. However, in the stentless valve, the leaflet support structure is less rigid such that the entire support structure must be secured to other anatomical structures, such as the wall of a blood vessel, to prevent the valve from collapsing against the fluid pressure. If the support structure is supported by attachment to other structures, the leaflets will have proper coaptation. The support structure can comprise the polymer of the leaflets or other flexible material in a generally cylindrical configuration that defines the commissure supports and the scallops or other suitable interface that hold the attached edges of the leaflet. The flexible support structure generally is sutured or otherwise attached to the wall of the corresponding blood vessel or other structure.

The polymer leaflets are configured to flex in response to changes in blood flow. In particular, preferred embodiments of the valves function as one way check valves that open to allow flow in a desired direction and close in response to pressure differentials. Thus, when blood is flowing downstream, the leaflets fully open to allow for flow through the valve.

When the valve closes in response to pressure differentials, the free edges of adjacent leaflets contact in the closed configuration with the leaflets extending across the lumen. The contact of adjacent leaflet free edges across the lumen of the valve eliminates or greatly reduces back flow through the valve. The contacting portion of the leaflets is referred to as the coaptation region.

The leaflets are formed from a thin film of flexible polymer. Suitable polymers are biocompatible, in that they are non-toxic, non-carcinogenic and do not induce hemolysis or an immunological response. Heart valve prostheses formed from polymers preferably are non-thrombogenic. Relevant mechanical properties of polymers include, for example, stiffness, strength, creep, hardness, fatigue resistance and tear resistance. Preferred polymers are durable in that they do not significantly lose their flexibility and do not significantly lose their mechanical strength following many years of use.

Figure 2:
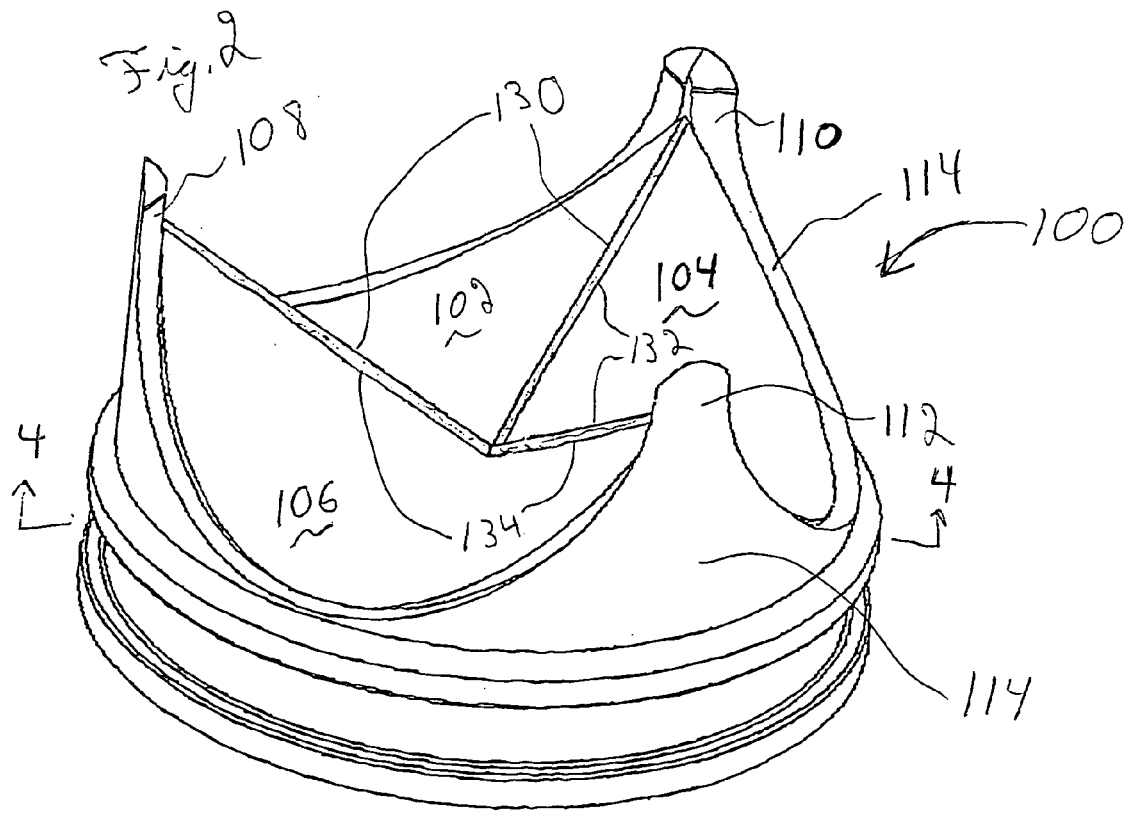
FIG. 2 is a perspective view of a heart valve prosthesis with reinforced polymer leaflets, wherein the valve is in a closed configuration.
Figure 3:
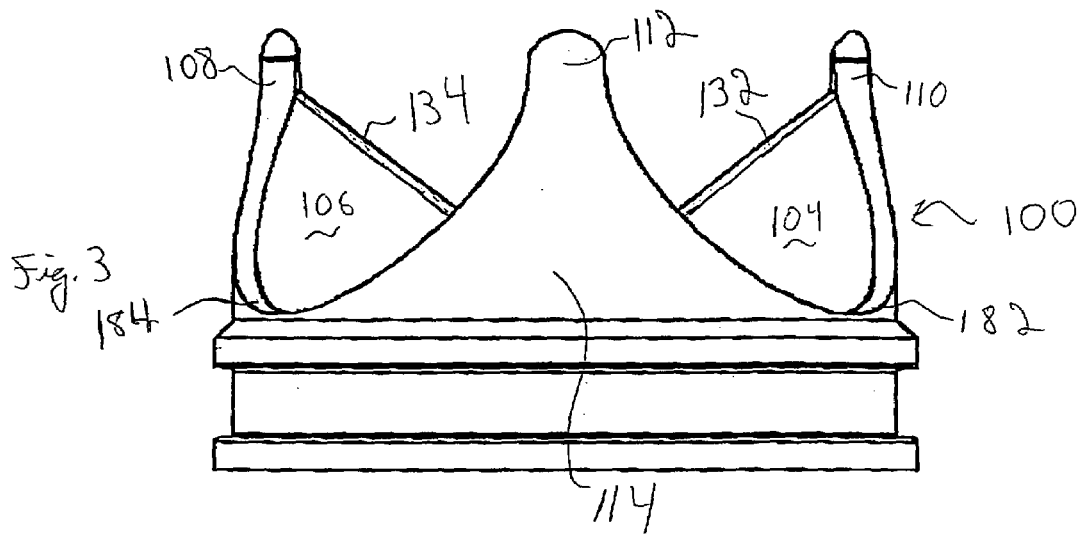
FIG. 3 is a side view of the prosthesis of FIG. 2.
Figure 4:
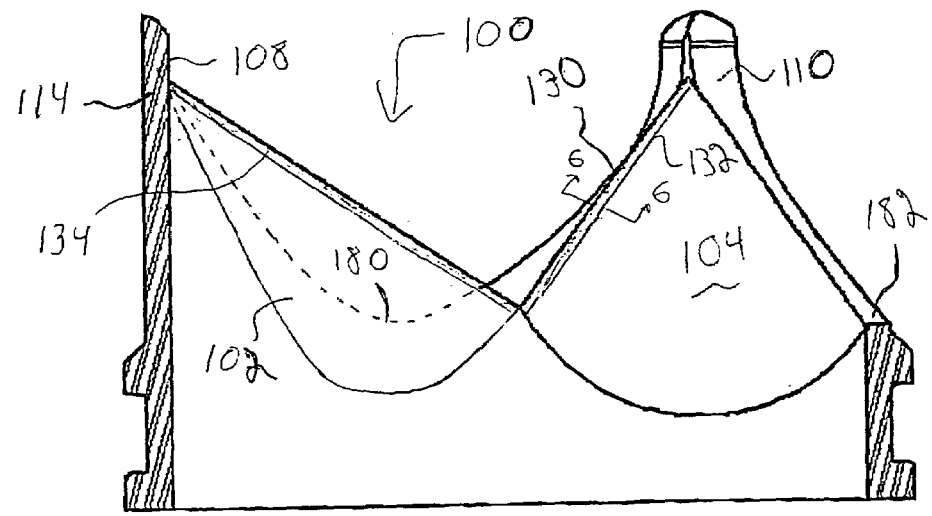
FIG. 4 is a sectional view of the prosthesis of FIG. 2 taken along line 4—4.

Generally, polymer leaflets can be formed by a variety of casting and molding processes. In preferred embodiments, the leaflets are formed by dip coating a mandrel. The surface of the mandrel is contoured to create a surface to which the leaflets conform when a thin polymer layer is applied to the mandrel, generally by dip coating. The mandrel is machined to generate the desired contours for the leaflets. As removed from the mandrel, the leaflet has its relaxed state with no stress or tension. This relaxed state can correspond to an almost closed leaflet configuration, a fully open leaflet configuration or a partially open leaflet configuration. In the almost closed configuration, there preferably is a small top surface along the top of the mandrel separating the leaflets that still forms an edge between the leaflet contours and the top of the mandrel. In a fully closed configuration, the contoured surfaces meet one another at the top of the mandrel and form the separation edges which correspond to the free edge of the leaflets. In preferred embodiments, the separation edges are sharp and have a small angle similar to the preferred edges in embodiments with edges separating the top of the mandrel from the contoured mandrel surfaces. The mandrel for the fully closed configuration has a structure corresponding to the closed leaflet configuration, as shown in FIGS. 2–4. In use, the valve flexes between a fully open configuration and a closed configuration. Each selection of the relaxed state of the polymer leaflets has particular advantages.

The valve includes a plurality of leaflets. Preferred valves have three leaflets. The leaflets are supported at the attached edge by the support structure, for either stented or stentless valves. The attached edge of the leaflet follows along the commissure supports and the scallops of the support structure. The leaflets flex between the open and closed configurations according to the constraints provided by the attached edge.

In some preferred embodiments, the leaflets are formed directly in association with the corresponding leaflet support structure, either a stent or a flexible support structure. In these embodiments, the support structure is coated with the polymer along with the mandrel during the coating process. Thus, a composite structure comprising the support structure and the polymer leaflets is removed from the mandrel as a unit. A complex step involving the association of the polymer leaflets with a support structure is avoided. A flexible support structure connected to the leaflets generally also is formed from the same polymer as the leaflets during the dip coating process if no separate support structure is mounted on the mandrel.

In alternative embodiments, a supplemental leaflet support structure is attached to the polymer leaflets and a flexible support structure associated with the leaflets after removal of the polymer structure from the mandrel. For example, to produce a stented valve, the leaflets can be formed with a flexible support comprised of the same material as the leaflets that are subsequently attached to a rigid stent after being removed from the mandrel. Placement of the stent on the mandrel prior to dip coating avoids the complication of attaching the leaflets to the support structure after removing the leaflets from the mandrel.

In preferred embodiments, the mandrel is designed to greatly facilitate the processing of the polymer leaflets. In particular, the mandrel has an edge forming a boundary between the surface of the mandrel corresponding to the body of the leaflets and a top surface of the mandrel. The edge on the mandrel forming the free edge of the leaflets preferably has a small radius of curvature such that the edge is sharp. This edge provides a clear demarcation indicating the desired free edge of the leaflets, and a preferred sharp edge forms a separation point for the polymer that results in the free edge of the leaflet. The presence on the mandrel of a sharp edge corresponding to the free edge of the leaflet provides efficient approaches to forming the finished edge of the leaflet. Furthermore, the finished edge of the polymer leaflet is less susceptible to defects at the free edge and has a well defined separation line determined by the mandrel.

Specifically, if the edge of the mandrel is sharp, the free edge of the leaflet can be formed along the sharp edge of the mandrel by removing the polymer on the top of the mandrel without any mechanical cutting along the sharp edge. This separation at the sharp edge by removing the polymer along the top of the mandrel forms the free edge without necessarily needing further processing. A groove can be placed along the edge to thicken the polymer at the free edge. This thickening of the polymer reinforces the free edge.

While the radius of curvature must be small to produce a sharp edge, the angle between the leaflet surface and the top of the mandrel also must not be too large. While the top of the mandrel can be slightly convex, at a large enough angle at the edge, the polymer will not pull apart easily when removing the polymer at the top of the mandrel even if the radius of curvature is small.

In preferred embodiments, the radius of curvature and the angle are selected appropriately such that the polymer separates along the edge without putting excessive stretching force on the polymer. Specifically, the discontinuity at a sharp edge results in a thinner polymer film at the edge that breaks when stress is applied. The thin polymer at the edge is stretched beyond its elastic limit without applying significant stress to the remainder of the polymer.

The shape of the top of the mandrel away from the free edge is irrelevant to obtaining the sharp edge. Therefore, the mandrel can have various shapes along the top of the mandrel away from the free edge as long as the boundary edge has a small radius of curvature and a small angle between the top surface and the contoured surface near the sharp edge. Some specific shapes for the top of the mandrel are described below.

In a simple embodiment of the dip coating process, the mandrel is dipped a single time into a polymer composition that subsequently solidifies on the mandrel to form a polymer structure with the polymer leaflets. In alternative embodiments, leaflet formation can involve multiple dips of the mandrel into one or more polymer compositions, as described further below. Reinforcements, support structures and other structural elements can be placed onto the mandrel prior to dip coating, between dip coating steps or following dip coating. In alternative embodiments, flexible support structures are formed from the same polymer material as the leaflets during the dip coating process.

Following completion of the dip coating process, the polymer is allowed to dry by evaporation of the solvent to form a solidified polymer structure. The polymer can be heated to speed solvent evaporation. If the polymer was dipped into a polymer melt, cooling of the polymer on the mandrel solidifies the polymer structure. Preferably, the solidified polymer over the top surface of the mandrel is removed to form the free edge of the leaflet. Once the free edge of the leaflet is formed, the polymer structure is removed carefully from the mandrel.

The polymer structure separated from the mandrel can be processed into the complete valve prosthesis. In preferred embodiments, a support structure is placed over the mandrel prior to performing the dip coating. Therefore, the composite of the polymer film and support structure are removed as a unit from the mandrel. If necessary, the bottom of the polymer structure can be trimmed and/or secured to the support structure. In alternative embodiments, the polymer structure can be placed in contact with a support structure or an additional support structure after removal from the mandrel. The polymer structure can be attached with glue or the like to a support structure. A sewing ring may be attached to the base of the polymer structure or a support structure to provide for attachment/implantation of the valve.

Valved Prostheses

The improved polymer leaflets can be used in valved prostheses. In particular, the leaflets can be used in artificial hearts, heart valve prostheses, valved vascular prostheses or left ventricular assist devices. The polymer leaflets open and close to control flow through the valve.

Heart valve prostheses with polymer leaflets are suitable for the replacement of damaged or diseased native heart valves. While the embodiments of the heart valve prosthesis shown in the figures below have three polymer leaflets, heart valve prostheses can be constructed with different numbers of polymer leaflets, such as two leaflets, four leaflets or more than four leaflets. The prosthesis may or may not have the same number of leaflets as the natural valve that it is used to replace.

Mammalian veins include valves that assist with blood circulation by limiting the amount of back flow in the veins. Veins collect blood from capillaries and are responsible for returning blood to the heart. Generally, vascular valves are replaced as part of a vascular graft with sections of conduit.

Mammalian hearts have four major valves. With appropriate sizing and attachment, the polymer valves of the present invention are suitable for replacement of any of the heart valves. Polymer heart valve prostheses for replacement of the mitral and tricuspid valves generally include rigid stents.

An embodiment of a heart valve prosthesis with flexible polymer leaflets is shown in its fully open position in FIG. 1. Heart valve prosthesis 100 includes leaflets 102, 104, 106, commissure supports 108, 110, 112, support structure/stent 114 and sewing ring 116. Heart valve prosthesis 100 with closed polymer leaflets is shown in FIGS. 2–4. Leaflets 102, 104, 106 contact the respective adjacent leaflets to close the opening of the valve.

Sewing ring 116 is used to attach valve 100 to the patient's tissue annulus or to other portions of a prosthesis. Support structure/stent 114 can be relatively rigid, such that the support structure functions as a stent to maintain leaflet function with attachment to the patient only at base 142 of support structure 114. Alternatively, support structure 114 can be less rigid as part of a stentless valve, with support structure 114 being secured to other anatomical structures or other devices to maintain the leaflet function.

Referring to FIG. 1, support structure/stent 114 includes commissure supports 108, 110, 112 and scallops 120, 122, 124 between the commissure supports. Free edges 130, 132, 134 of leaflets 102, 104, 106, respectively, join at the commissure supports 108, 110, 112. Attached edges 136, 138, 140 of leaflets 102, 104, 106 also secure to the support structure along scallops 120, 122, 124. The base of support structure 114 generally is a cylindrical ring 142 that forms the opening into the valve at the upstream or proximal end of the valve.

Sewing cuff 116 generally extends from base 142 of support structure 114. Sewing cuff 116 facilitates the attachment of the heart valve prosthesis to the patient or device. Sutures, staples and/or other fastening mechanisms are passed through the sewing cuff to secure sewing cuff 116 to the patient's tissue annulus, to a conduit prosthesis or to other portions of a prosthesis. Sewing cuff 116 preferably extends outward from base 142 so that the fastening mechanism can be conveniently passed through sewing cuff 116 to attach the valve without significant risk of piercing leaflets 102, 104, 106.

Figure 5:
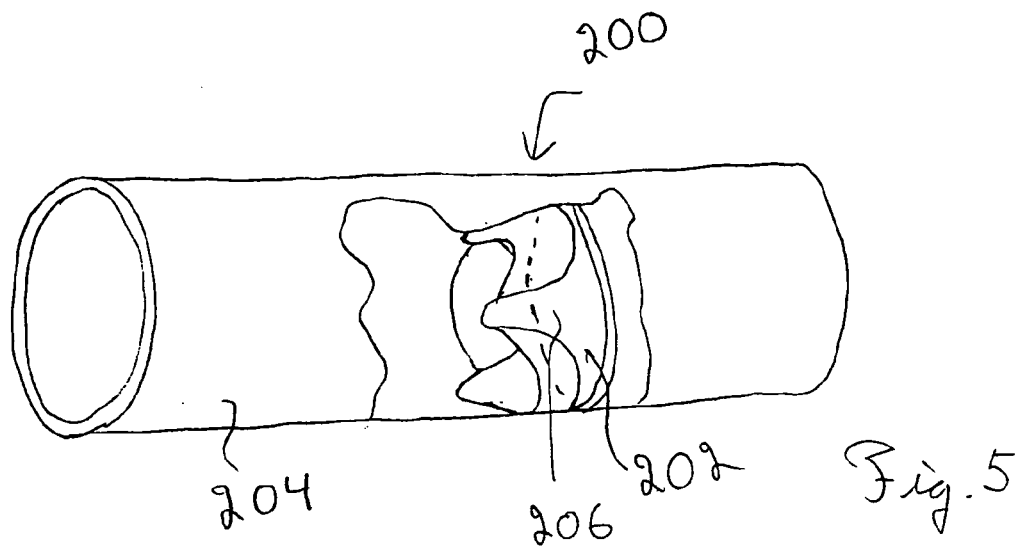
FIG. 5 is a cut away perspective view of a vascular prosthesis incorporating a valve having polymer leaflets in which a portion of the prosthesis has been removed to expose the valve.

The valve prosthesis can be incorporated into a vascular graft with a conduit for replacement of a venous valve or for the replacement of an aortic or pulmonary heart valve. A valved venous prosthesis 200 is shown in a fragmentary view in FIG. 5. Prosthesis 200 includes a three leaflet polymer valve 202 in a conduit 204. Support structure/stent 206 can be rigid or flexible, as discussed above, with corresponding appropriate attachment to conduit 204. For example, if support structure/stent 206 is flexible, the leaflet support is attached to conduit 204 for support. Conduit 204 can be made from natural materials, such as fixed bovine pericardium, or synthetic materials, such as polymers, for example, polyesters.

Figure 6:
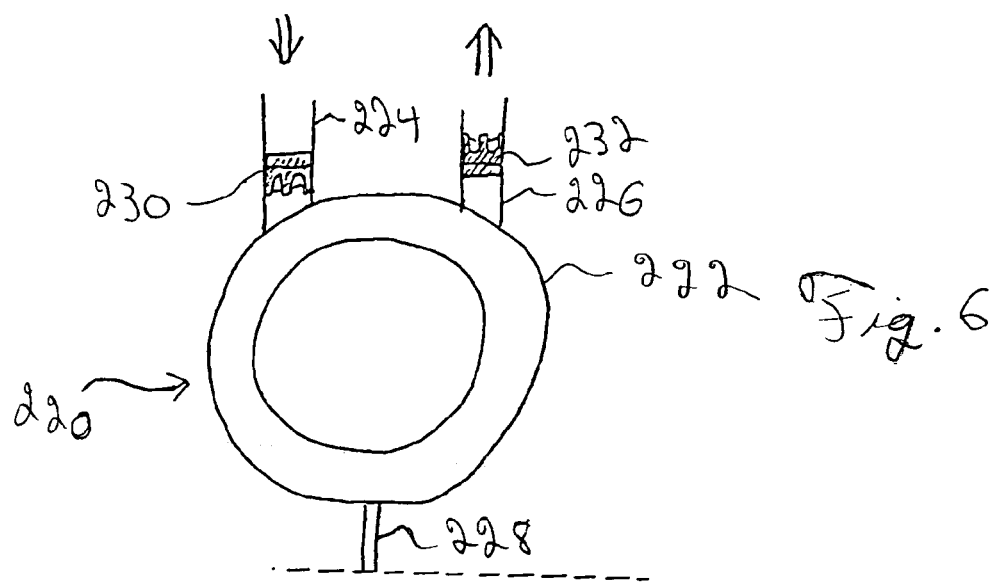
FIG. 6 is a fragmentary side view of a left ventricular assist device with polymer valves, in which the sides of the inflow and outflow tubes have been removed to expose the inflow and outflow valves.

In addition, a polymer valve as described herein can be incorporated into a left ventricular assist device 220, as shown in FIG. 6. Left ventricular assist devices are implanted devices generally used to maintain the ventricular pumping function of a patient with a damaged or diseased heart awaiting a heart transplant. Left ventricular assist device 220 includes a drive unit 222, an inflow tube 224, an outflow tube 226 and connection 228. Drive unit 222 includes a pump to provide pulsatile flow from inflow tube 224 to outflow tube 226. Connection 228 provides for electrical or pneumatic control signals to be directed to the drive unit from a controller and power supply, generally external to the patient. Inflow tube 224 includes an inflow valve 230, and outflow tube 226 includes an outflow valve 232. Arrows depict the blood flow through inflow tube 224 and outflow tube 226 as controlled by valves 230, 232. Either one or both of inflow valve 230 and outflow valve 232 can be a polymer valve as described herein.

For any of the prosthetic valve embodiments, if the support structure/stent 114 is formed from a rigid material that supports the leaflets, suitable rigid materials include, for example, rigid polymers, metals, ceramics, carbon materials and combinations thereof. Suitable rigid polymers include, for example, polyacetals, such as Delrin® and Celcon®, polysulfones, polyethersulfones, polyarylsulfones, polyetherether-ketones, and polyetherimides. Suitable metals include biocompatible metals, such as, stainless steel, titanium, cobalt alloys, such as Elgiloy®, a cobalt-chromium-nickel alloy, and MP35N, a nickel-cobalt-chromium-molybdenum alloy, and Nitinol, a nickel-titanium alloy. Heart valve stents made from spring metals, such as Elgiloy®, exhibit good mechanical properties, such as strength and fatigue endurance, and can have a smaller cross-section than corresponding polymer stents. Composite metal/polymer heart valve stents are described in copending and commonly assigned U.S. patent application Ser. No. 09/475,721 to Reimink et al., entitled "MEDICAL DEVICES WITH POLYMER/INORGANIC SUBSTRATE COMPOSITES," incorporated herein by reference. In addition, stents can be produced from ceramic materials, such as pyrolytic carbon, silicon carbides or metal carbides, hydroxyapatite and alumina. Suitable stents can also be produced from carbons such as graphite. Composites suitable for stents that advantageously combine pyrolytic carbon and carbides are described in copending and commonly assigned U.S. patent application Ser. No. 09/460,140 to Brendzel et al., entitled "Pyrolytic Carbon and Metal/Metalloid Carbide Composites," incorporated herein by reference.

Support structures that are flexible can be produced, for example, from flexible polymers or metals. Suitable flexible polymers include, for example, polyurethanes, polydimethyl siloxane and polytetrafluoroethylene. Flexible support structures generally can be produced from the same flexible polymer as the leaflets, a different flexible polymer or a combination thereof. To form the support structure, the flexible polymer can be formed into a sheet, woven into a fabric or produced by a variety of other approaches.

Suitable flexible polymers for support structures also include resorbable polymers, such as, dextran, hydroxyethyl starch, gelatin, derivatives of gelatine, polyvinylpyrrolidone, polyvinyl alcohol, poly [N-(2-hydroxylpropyl) methacrylamide], polyglycols, polyesters, poly (orthoesters), poly(ester amides), and polyanhydrides. Resorbable polyesters include, for example, poly (hydroxy acids) and copolymers thereof, poly(E-caprolactone), poly (dimethyl glycolic acid), and poly (hydroxy butyrate). Preferred resorbable polymers include, for example, D, L-polylactic acid, L-polylactic acid, poly(glycolic acid), and copolymers of L-lactic acid, D-lactic acid and glycolic acid. The formation of heart valve stents from resorbable polymers is described further in U.S. Pat. No. 5,728,152 to Mirsch II et al., entitled "Bioresorbable Heart Valve Support," incorporated herein by reference.

The leaflets can be formed separate from the support structure, or the leaflets can be formed directly in association with the support structure. If the leaflets are formed separate from the support structure, they can be attached to the support structure by an approach suitable for the particular materials of the components. For example, polymer leaflets can be connected to suitable support structures by heat bonding, suture, adhesive bonding or the like. The leaflets can be formed in direct association with the support structure whether or not the support is formed from the same material. If the leaflets are formed directly in association with the support structure, the support is incorporated into the process for leaflet formation, as described below.

Sewing cuff 116 can be produced from natural material, synthetic material or combinations thereof. Suitable natural materials for sewing cuff 116 include, for example, fixed/ crosslinked tissue, such as bovine or porcine pericardial tissue. Crosslinking of tissue provides mechanical stabilization, for example, by preventing enzymatic degradation of the tissue. Crosslinking of tissue also removes antigenic sites that could result in the patient's rejection of the bioprosthesis. Glutaraldehyde or formaldehyde typically is used for fixation, but other fixatives can be used, such as epoxides, genipin, polyimides and other difunctional aldehydes.

Suitable synthetic materials for sewing cuff 116 include flexible polymers, generally woven into a fabric. Preferred materials include, for example, polyesters, or polytetrafluoroethylene. Fabric sewing cuffs can include antimicrobial metals or other antimicrobial agents to reduce the incidence of infection following implantation of the prosthesis into the patient.

Leaflet Structure and Composition

In bioprostheses, flexible leaflets are designed to approximate native leaflet function. While these leaflets are flexible, they must have a well defined and stable configuration to properly close at each cycle to prevent back flow. Also, the leaflets should be durable to provide stable performance over many years of use.

Suitable polymeric materials for formation into the leaflets include, for example, synthetic polymers as well as purified biological polymers and combinations thereof. Flexible polymers include elastomers and other polymers that can sustain significant flexure, bending, twisting, wear and/or deformation without structural failure. Appropriate synthetic polymers include, without limitation, polyamides (e.g., nylon), polyesters, polyacrylates, vinyl polymers (e.g., polyolefins, polyethylene, polytetrafluoroethylene or other halogenated polymers, polypropylene, ethylene-propylene copolymers, ethylene-propylene-diene monomer copolymer (EPDM) and polyvinylchloride), polycarbonates, polyacetals (e.g., Delrin®), polyurethanes, polydimethyl siloxanes, cellulose acetates, ethylene vinyl acetates, polysulfones, nitrocelluloses, derivatives thereof, similar copolymers, and mixtures thereof. Particularly preferred flexible polymer materials for the formation of flexible polymer heart valve leaflets include, for example, polyurethanes, polydimethyl siloxanes, polytetrafluoroethylenes, derivatives thereof and mixtures thereof.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Preferred polymers are biocompatible. In preferred embodiments of flexible leaflets, the polymer leaflets generally have a thickness from about 50 microns to about 1000 microns and more preferably from about 100 microns to about 300 microns. A flexible polymer used to form the leaflets of heart valve prostheses is preferably a polymer that has sufficient durability to withstand the repeated cycling required for replacement heart valve use. For a human patient, the valve must cycle about 40 million times each year, and the valve ideally remains functional over the remaining natural expected lifetime of the patient. Current tissue valves may require replacement following about 400 million to about 600 million cycles. Therefore, the polymer substrate preferably can withstand at least about 400 million cycles and more preferably can withstand more than about 600 million cycles without significant structural deterioration. Polyurethanes and silicone polymers are particularly preferred for achieving these performance requirements.

The polymer leaflets flex between a generally fully open position and a generally closed position. In the open position, the free edges of the polymer leaflets form the downstream opening of the valve and do not significantly resist forward blood flow. In the closed position, the free edges of adjacent leaflets contact in the coaptation region to close the valve and do not allow significant leakage.

While the leaflets flex between the open position and the closed position in use, the leaflets have a natural relaxed position when no forces are applied. When the leaflets are formed on a mandrel, the shape of the mandrel corresponds to the relaxed position of the leaflets since the polymer forms on the mandrel from a liquid without the application of any stresses to the polymer. By adjusting the shape of the mandrel, the relaxed position of the leaflets can be selected to have a desired shape.

In particular, the relaxed state of the leaflets corresponding to the mandrel shape can approximate a fully open position of the valve such that the polymer material is under little, if any, stress in the fully open position. Alternatively, the leaflets can have a relaxed position corresponding to an almost closed valve. In other alternative embodiments, the leaflets can have a relaxed position intermediate between the open position and the closed position. The processing of the valves to form the prosthesis is similar regardless of the relaxed configuration of the leaflet, except for the machining of the mandrel to produce the desired relaxed position of the leaflets.

The polymer leaflets can include one or more reinforcements to strengthen the leaflet. The reinforcement can be formed as a thickening of the flexible polymer or as an additional composition bonded to the flexible polymer forming the body of the leaflet, with or without thickening the leaflet. The reinforcement can be localized or can extend over a significant portion of the leaflet area.

Figure 7:
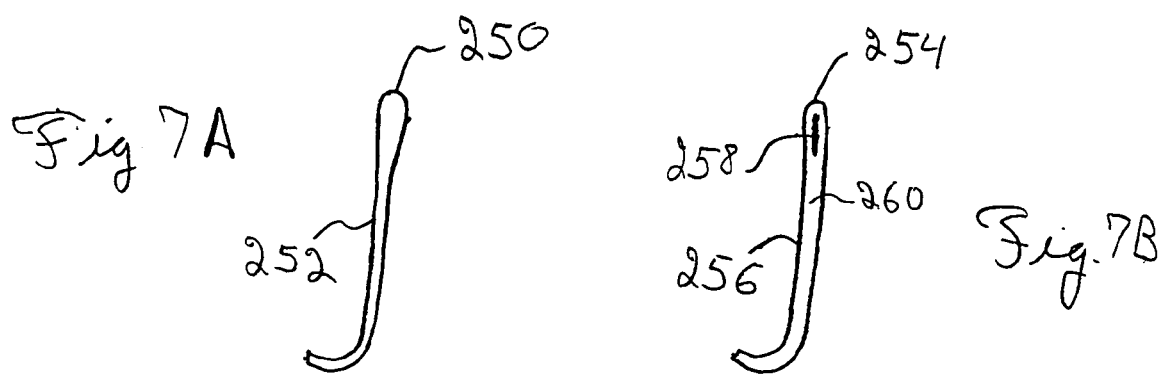
FIG. 7A is a sectional view of one embodiment of a reinforced polymer leaflet with a thickening of the leaflet at the coaptation edge, the cross section being taken through the center of the leaflet.
FIG. 7B is a sectional view of an alternative embodiment of a reinforced polymer leaflet with a reinforcing member near the free edge of the leaflet, the cross section being taken through the center of the leaflet.
FIG. 7C is a sectional view of an alternative embodiment of a reinforced polymer leaflet with a reinforcing layer, the cross section being taken through the center of the leaflet.

In some preferred embodiments, the free edge of the leaflet is reinforced. Referring to FIG. 7A, free edge 250 of leaflet 252 is thickened to reduce the possibility of tearing or other damage of the free edge. Referring to FIG. 7B, free edge 254 of leaflet 256 includes a reinforcing member 258 with a different composition than body 260 of the leaflet. The reinforcing member may or may not result in a thickening of the free edge relative to the body of the leaflet. If the free edge has a local reinforcement as shown in FIGS. 7A and 7B, additional reinforcements can be included away from the free edge. Referring to FIG. 7C, a reinforcing member 262 is located throughout the body of leaflet 264. Reinforcing member 262 generally has a different composition than the flexible polymer comprising the remainder of the body of the leaflet.

Reinforcing members preferably are formed from polymer films, perforated polymer films or fabrics. The reinforcing members preferably are relatively flexible and generally have a greater strength than the flexible polymer forming the remainder of the leaflet body. A variety of other reinforcement structures and compositions can be used. Polymer leaflet reinforcements are described further in copending and commonly assigned U.S. patent application Ser. No. 09/666,823 to Woo et al., entitled "Valved Prostheses With Reinforced Polymer Leaflets," incorporated herein by reference.

The mandrel can have a groove adjacent to the sharp edge along the surface corresponding to the leaflet free edge to provide for additional thickening along the free edge of the leaflet, as described further below. When forming the free edge of the leaflet, the removal of the polymer at the top of the mandrel can be performed while preserving the thickening of the polymer adjacent the sharp edge. This thickening at the sharp edge can be combined with the use of a reinforcing member to provide additional reinforcement of the leaflet.

Use of the processing approaches based on the improved mandrel design result in polymer leaflets with more consistent properties. In particular, if the polymer is separated along a sharp edge, the free edge of the leaflets is defined reproducibly by the mandrel sharp edge. In contrast, approaches in which the top of the leaflets are cut according to predetermined measurements result in variation in the precise position of the leaflet free edge due to limitation in measurement and due to potential stretching of the polymer during the cutting process. Also, the edges can be torn by cutting using standard approaches. Thus, improved uniformity between leaflets on different valves is a result of using the improved processing approaches described herein.

In summary, the formation of polymer leaflet valves using mandrels with suitably placed sharp edges, provides for a more efficient and cost effective process for creating polymer leaflet valves. The process also results in very high consistency/repeatability for forming high quality leaflets and valves while eliminating the potential introduction of defects along the free edge of the leaflet.

Mandrel Structure

The improved mandrels have an edge corresponding to the free edge of the leaflets of the valve. In preferred embodiments, the edge has a small radius of curvature, i.e., a sharp edge, on the mandrel corresponding to the free edge of the leaflets. In addition, the edge preferably has an angle not too large, approximately 135 degrees or less, between the two surfaces joined at the edge. With edges having preferred sharpness and angles, the polymer pulls apart or separates at the sharp edge without the need to apply excessive force. Preferred values of angle may depend on the sharpness of the edge and vice versa. For these preferred embodiments, the top of the mandrel has a shape consistent with having a sharp edge forming an angle that is not too large to mark the boundary of the free edge of the leaflet. The polymer coated onto the top of the mandrel can be easily and efficiently separated to produce a free leaflet edge with a high degree of uniformity between different valves.

Referring to FIG. 8, mandrel 300 has a generally cylindrical shaft 302 and a contoured portion 304. Cylindrical shaft 302 is used to grip mandrel 300 during the dip coating process. Cylindrical shaft 302 can have other shapes and/or structural features, such as appendages, holes or cavities, to facilitate the gripping process. Generally, the cylindrical shaft can be connected to an automated apparatus to lower the mandrel in a reproducible manner into the polymer coating material during the dip coating process.

Contoured portion 304 is formed to produce structures with appropriate shapes to generate desired features in the polymer cast on the surface of the mandrel. Referring to FIG. 8, contoured portion 304 includes a plurality of ridges 306 corresponding to commissure supports of the polymer valve. Scallops 308 connect between ridges 306. Scallops 308 correspond with scallops extending between the commissure supports in the support structure. Contours 310 are formed between ridges 306 and scallops 308. The leaflets are formed on contours 310. The attached edge of the leaflets follows the commissure support and scallops of the valve, which correspond to ridges 306 and scallops 308 on mandrel 300. Edge 312 forms a boundary between contours 310 and top surface 314 of mandrel 300.

Ridges 306 mark the end point of the free edges of the leaflets and the separation between adjacent leaflets. Ridges can have various shapes, as desired, to correspond to desired valve performance characteristics. A support structure/stent can be attached to the mandrel along ridges 306 prior to performing the dip coating. If the polymer structure is attached to a support structure following removal from the mandrel, polymer along the ridges is associated with at least a portion of the commissure supports separating adjacent leaflets. Ridges 306 help to provide proper coaptation of the closed leaflets. The ridges may include additional features, such as structure for the mounting of leaflet support structures. The thickness of the ridge separating adjacent leaflets generally is selected as appropriate for the desired prosthesis structure.

Contours 310 are machined to provide a desired shape for the leaflets in their relaxed position. As shown in FIG. 8, the leaflets have a shape approximating their fully open position. In alternative embodiments, the leaflets are formed in a relaxed configuration corresponding to a partially closed valve. In these embodiments, contours 310 are designed to produce a smaller top surface 314. The contours can be formed to approximate a closed configuration of the valve.

In alternative embodiments, a groove 316 is located adjacent edge 312, as shown in FIG. 9A. Groove 316 allows a thickening of the polymer along the free edge of the leaflet. In preferred embodiments, groove 316 is generally parallel with edge 314 on contour 310, as shown in the expanded view in FIG. 9B. The depth (D) of groove 316 from contour surface 310 preferably is from about 0.01 mm to about 1 mm and preferably from about 0.05 mm to about 0.5 mm. Groove 316 preferably is next to edge 312, but may be located away from top surface 314. The point of maximum depth of groove 316 is a distance "Z" from top surface 314. Distance Z preferably ranges from about three times the radius of curvature at the edge to about 5 mm, and more preferably from about three times the radius of curvature at the edge to about 2 mm. Groove 316 can have any shape, such as, rounded, square, complex, etc.

Edge 312 preferably has sufficient sharpness at an angle that is not too large to provide easy separation of the polymer along top surface 314 of the mandrel from the polymer along contours 310. While an edge may appear infinitely sharp on a casual examination, a closer inspection shows the edge has a curve connecting contours 310 and top surface 314. The sharpness is defined by the radius of curvature at the edge while the angle refers to the angle formed between contour 310 and top surface 314 at edge 312. In preferred embodiments, a sharp edge results if the radius of curvature is no more than about 0.25 mm, and preferably no more than about 0.15 mm and even more preferably no more than about 0.1 mm.

In preferred embodiments, the angle at the edge is less than about 135 degrees, preferably less than about 105 degrees and more preferably less than about 90 degrees. The angle at the edge, however, is difficult to specify with absolute precision because there is no unequivocal division between top surface 314 at edge 312 and contour 310 at edge 312. The angle can be evaluated in a plane normal to the sharp edge of the mandrel by ignoring the curvature at the edge visible by magnification of the sharp edge. The presence of a groove does not effect this evaluation of the angle since the edge can then be formed at the top of the groove separating the groove from the top of the mandrel.

The angle and sharpness of the edge may not be uniform at all points along the edge. In preferred embodiments, the angle and sharpness fall within the preferred ranges at all points along the edge. However, the angle and sharpness can deviate from preferred values over small sections of the edge without affecting the processing of the polymer structure.

In one preferred embodiment, the top of ridges 306 are along the top of contours 310 such that the top of ridges 306 meet edge 312 at a point where the free edge of the leaflet connects with the attached edge. The tops of the ridges are at the same height as the free edge of the leaflet.

In some embodiments, edge 312 is not necessarily in a plane. However, if edge 312 is in a plane, the top of ridges 306 are preferably in the same plane. Referring to FIG. 10, an embodiment of a mandrel is shown having edges that are not in a plane. Mandrel 324 has leaflet contours 326, 328, 330 forming an edge 332 at the intersection with top surface 334 of mandrel 324. The radius of curvature and angle can be evaluated at any point along the edge.

Referring to FIG. 8, top surface 314 of mandrel 300 can have any shape consistent with producing an edge 312 with the desired characteristics. To establish a desired angle at edge 312, the mandrel can have, for example, a flat surface, a convex surface, a slightly concave surface or a more complex shape along the top of the mandrel. One convenient structure for top surface 314 consistent with the formation of a sharp edge 312 is a flat top.

Figure 11:
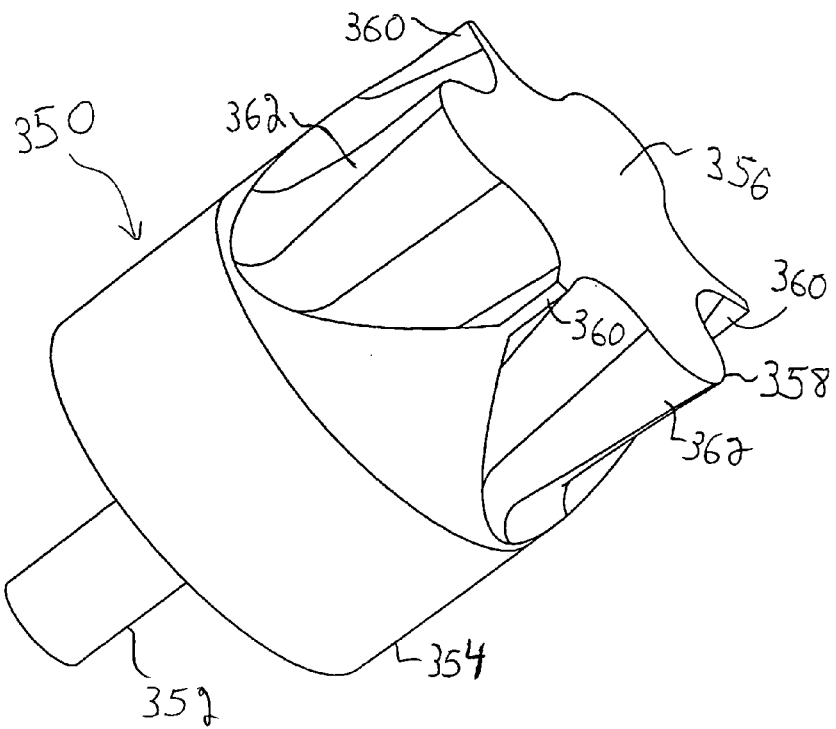
FIG. 11 is perspective view of a mandrel with a planar top surface.

An embodiment of a mandrel with a flat top surface is shown in FIG. 11. In this embodiment, mandrel 350 has a shank 352 extending from cylindrical section 354. Mandrel 350 has a flat top surface 356 outlined by an edge 358. Flat top surface 356 extends over ridges 360. Edge 358 extends along the top of ridges 360 and along the top of contours 362.

While a flat top surface, a slightly concave surface or a convex surface are appropriate structures for the top of the mandrel to yield the sharp boundary edge, alternative top surface structures are consistent with forming the sharp edge. Specifically, the shape of the top of the mandrel away from the free edge generally is irrelevant to obtaining the processing and structural advantages. Regardless of the shape, however, the boundary edge preferably has a small radius of curvature and angles within desired ranges.

Figure 12:
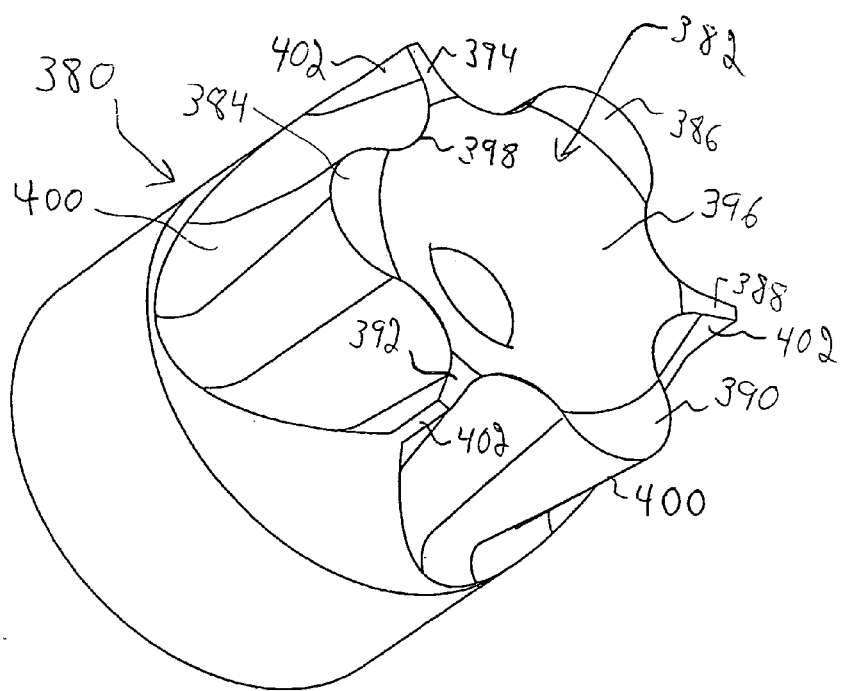
FIG. 12 is a perspective view of a mandrel with a top surface having planar portions and a concave portion.

An alternative embodiment of the mandrel is shown in FIG. 12. In this embodiment, mandrel 380 has a top surface 382 with flat portions 384, 386, 388, 390, 392, 394 and a concave central portion 396. A continuous edge 398 is formed that extends along the top of contours 400 as well as along the top edges of ridges 402. Edge 398 extends along flat portions of top surface 384 as well as concave portion 396.

Another alternative embodiment of a mandrel is shown in FIG. 13. Mandrel 420 has a top surface 422 with flat portions 424 and a protruding portion 426. Edge 428 extends along the outside of flat portions 424 and sections of protruding portion 426. Edge 428 forms the boundary between top surface 422 and both contours 430 and ridges 432. Protruding portion 426 includes a pointed tip 434 that breaks the surface of the polymer liquid to reduce the trapping of air during the dip coating process. Mandrel 420 includes a non-cylindrical shank 436 for gripping mandrel 420 during the dip coating process. Generally, the shank can have any desired shape, such as square or triangular.

The mandrel generally can be formed from one or more of various suitable materials including, for example, metals, polymers, ceramics and the like. The mandrel should be durable such that it can be used to produce a large number of uniform polymer valves before requiring replacement. The mandrel should be produced from a material that is inert and wetable with respect to the polymer liquid into which the mandrel is dipped during the dip coating process. Specifically, the mandrel should not chemically react or dissolve in the relevant polymer liquids. In addition, the mandrel is wetable if the polymer liquid easily spreads over the mandrel surface and forms a uniform coating. Also, the mandrel should be produced from a material that allows for easy separation of the dip coated polymer from the mandrel following solidification of the polymer, although a material can be covered by a permanent or temporary coating to facilitate polymer separation from the mandrel.

The mandrel can be formed from a plurality of materials in various configurations. For example, the body of the mandrel can be formed from a polymer material that is subsequently coated with a metal. In preferred embodiments, the mandrel is formed from a durable metal, such as stainless steel. Stainless steel is a preferred material for its wetting properties with polyurethane polymers and silicone based polymers. For preferred embodiments based on metal mandrels, the mandrels can be machined to form a mandrel with a desired surface shape, for example, using conventional machining approaches.

In the polymer dip coating processes, the mandrel preferably is dipped into a polymer liquid slowly. If the mandrel is made of a material wetable by the polymer liquid, the intermolecular attraction between the mandrel material and the polymer is larger than intermolecular attraction within the polymer liquid. Then, a layer of polymer liquid adheres to and spreads over the mandrel surfaces after the mandrel is removed from the polymer liquid. The polymer liquid takes the shape of the mandrel surfaces due to the stronger intermolecular attraction with the mandrel material. The polymer layer also has an interface with the ambient air or a vacuum at a free surface. The shape of the free surface is controlled by surface tension, which in turn is determined by the type of polymer liquid and the geometry of the mandrel.

The intermolecular attraction at the free surface is negligible compared with the intermolecular attraction in the polymer liquid. Molecules of the polymer liquid are attracted much more strongly by the molecules in the liquid than by air molecules at the free surface thereby creating surface tension. Surface tension tends to reduce the area of the free surface so that at equilibrium, the free surface has minimum surface energy.

On a conventional mandrel surface where the radius of curvature of the surface is much larger than the thickness of the polymer liquid layer, the polymer liquid tends to spread evenly in thickness over the surface contour. In contrast, when a mandrel surface has a sharp edge where the radius of curvature is comparable to the thickness of the polymer liquid layer, surface tension pulls the free surface toward the mandrel surface to reduce free surface area. The reduction of free surface area results in a thinner polymer layer around the edge. This reduction in polymer thickness at the edge is enhanced if the angle of the edge is also smaller because more free surface area is reduced from an otherwise uniform thickness layer. Having a smaller edge angle and/or a smaller edge radius yields a thinner polymer layer at the edge as well as a more localized area of thinning of the polymer layer.

Besides generating a thinner polymer layer at the edge, a small edge angle and small edge radius also concentrate stress at the edge when the solidified polymer layer is separated along the edge to remove the polymer on the top of the mandrel. Having a smaller edge angle and/or a smaller edge radius results in a higher concentration of stress at the edge. The combined effects of stress concentration and weakening/thinning at a sharp edge make it easier to separate two adjacent surfaces of the solidified polymer.

While the above discussion has focused on male mandrels, the dip coating process can similarly be performed with a female mandrel. A female mandrel is basically the inverse of a male mandrel, in which a void has the shape of a corresponding male mandrel. The polymer structure is formed on the inner surface, rather than the outer surface, of the mandrel. The resulting polymer structure has the identical shape as a polymer structure formed on the corresponding male mandrel with the shape of the void of the female mandrel. All of the same issues remain regarding the angle and sharpness of the edge separating the top of the mandrel from the leaflet contours. Thus, preferred embodiments can be evaluated by the properties of the edge.

Figure 14:
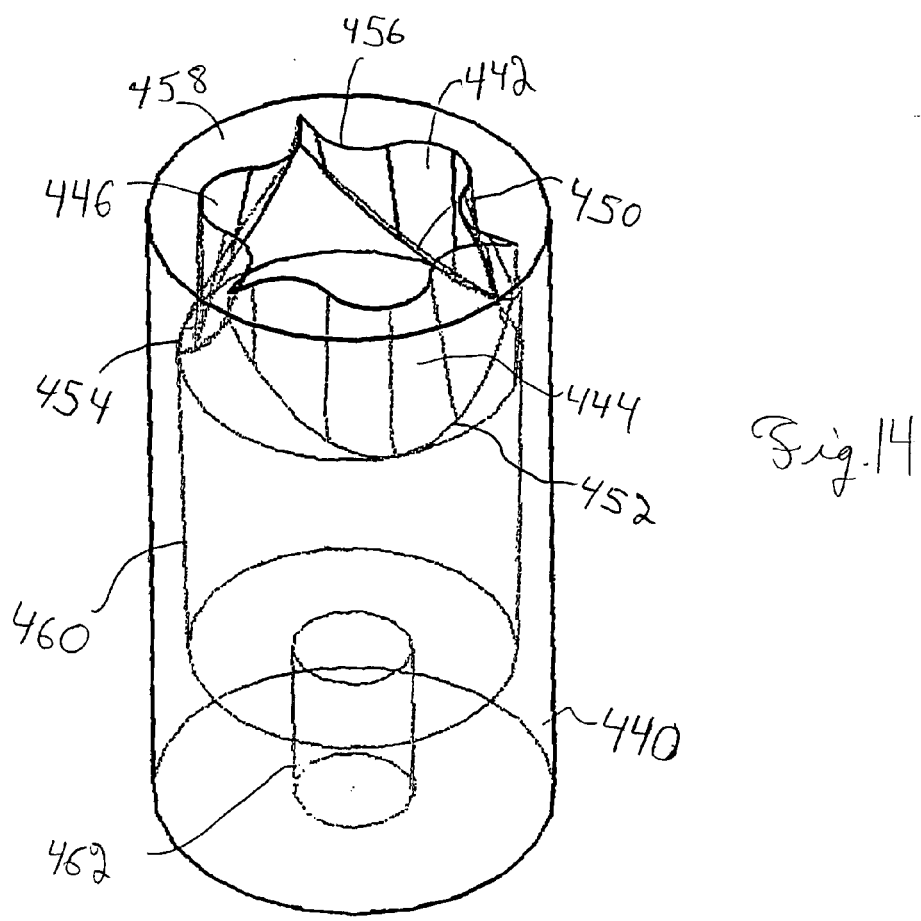
FIG. 14 is a perspective view of a female mandrel having a cavity contoured to form a polymer structure with a desired shape, hidden structure being shown for clarity.

An embodiment of a female mandrel is shown in FIG. 14, in which hidden structure is shown for clarity. Female mandrel 440 includes leaflet contours 442, 444, 446. Scallops 450, 452, 454 are located at the bottom of leaflet contours 442, 444, 446, respectively, and correspond to the attached edges of the leaflets. Edge 456 separates leaflet contours 442, 446, 448 from top surface 458 of mandrel 440. Top surface 458 can be flat or other suitable shape to yield desired sharpness and angle at edge 456. Cylindrical void 460 or a portion thereof can be used to form the base of the support structure. Hole 462 can be used for gripping mandrel 440 during the coating process.

Dip Coating Process

To form the polymer leaflets, the mandrels are preferably dip coated in a polymer liquid to cast the polymer on the surface of the mandrel. The polymer is solidified on the surface of the mandrel to form a polymer structure. In preferred embodiments, the mandrel has a sharp edge and a suitable angle at the sharp edge such that the polymer formed at the top of the mandrel separates from the remaining portions of the solidified polymer structure, including the polymer leaflets, by removing the polymer along the top surface without applying excessive force. After the free edges of the polymer leaflets are formed by removing the polymer along the top surface of the mandrel, the polymer valve structure is removed from the mandrel. The mandrel can be coated with a composition to facilitate removal of the polymer structure from the mandrel following complete solidification.

The process for forming the polymer valve structure is summarized in FIG. 15. A mandrel with a desired shape is dip coated 500 in a polymer liquid. After withdrawing the mandrel from the liquid, the polymer is solidified 502 partially or completely on the mandrel. Prior to dip coating or after dip coating before or after the polymer is solidified, optional reinforcements, such as fabric, can be placed 504 at desired locations along the mandrel. Before or after the polymer coating is solidified, an additional dip coating can be performed 506. Steps 500–504 can be repeated individually or collectively one or more times to obtain a desired polymer structure. After the final polymer structure is formed and the polymer is solidified, the polymer at the top of the mandrel is separated 508 from the remaining portions of the mandrel to produce the polymer valve structure. Then, the polymer valve structure is removed 510 from the mandrel. The formation of the prosthesis is completed 512.

A leaflet support structure/stent preferably is placed over the mandrel prior to dip coating to obtain a coating directly over the support structure. The support structure can be rigid, i.e., a stent, or flexible. If a leaflet support structure is placed over the mandrel, the polymer is simultaneously coated over the mandrel and the support structure material, such that the support structure material is formed as an integral structure with the solidified polymer. A strong composite of the polymer and the support structure can be formed. The support structure is preferably formed from a material that wets with the polymer solution. The polymer structure and support structure is removed from the mandrel as an integral unit.

Figure 16:
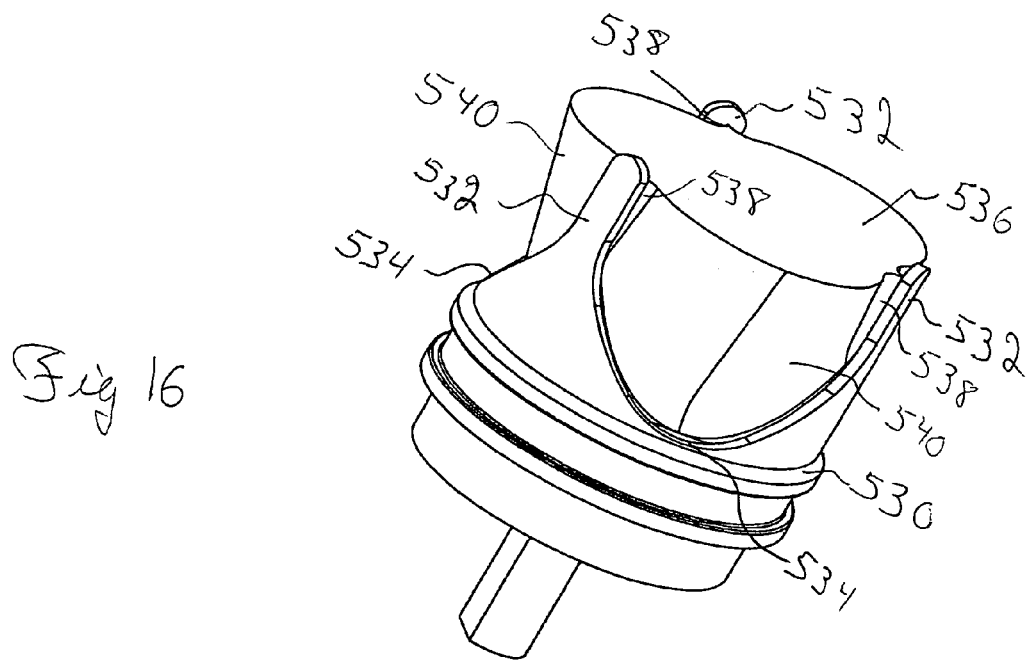
FIG. 16 is a perspective view of a mandrel with a leaflet support structure mounted on the mandrel.

A mandrel with a support structure is shown in FIG. 16. Support structure 530 includes commissure posts 532 and scallops 534. Commissure posts 532 contact mandrel 536 at ridges 538 separating leaflet contours 540. The contact points between mandrel 536 and commissure posts 532 and scallops 534 form the attached edge of the leaflets.

In alternative embodiments, a support structure can be formed on the mandrel from the same polymer as the leaflets during the dip coating process. In other alternative embodiments, the leaflets can be associated with the support structure/stent following removal of the leaflets from the mandrel. Generally, at least a portion of the leaflet support structure is formed in the dip coating process from the polymer used to form the leaflets, and this polymer support structure can be combined with one or more additional support structures/stents following completion of the dip coating process.

The polymer liquid used to perform the dip coating can be a polymer solution/dispersion or a polymer melt. Suitable polymers were described above. Suitable polymer solutions/dispersions comprise the polymer dissolved/dispersed in a solvent. The solvent can be selected based on the particular polymer. For polyurethanes, suitable solvents generally include, for example, N,N-dimethylacetamide (DMAC) and tetrahydrofuran (THF). The concentration of the solution can be selected to yield an appropriate viscosity and coating thickness. The coating thickness generally depends on the concentration and viscosity of the polymer solution. Desirable polymer concentration, i.e., solid content, generally range from about 1 weight percent to about 50 weight percent and more preferably from about 8 weight percent to about 30 weight percent, although desired values will depend on the composition of the polymer and the molecular weight of the polymer.

Polymer melts can be formed with polymers that can be heated to their melting points without decomposing. The viscosity generally will be dependent on temperature. The viscosity of the melt can be varied to obtain the desired coating thickness. Coating thickness generally is evaluated following solidification of the polymer. Desirable ranges of polymer leaflet thicknesses were given above.

To perform the dip coating the mandrel is connected to an instrument that lowers the mandrel a predetermined depth into the polymer liquid. The mandrel preferably is dipped slowly into the solution to avoid significant disruption of the solution. Speed of insertion and withdrawal can also effect the coating thickness with faster dipping resulting in a thinner polymer layer. In particular, for forming an initial polymer layer if multiple layers are applied, the first dip would preferably be slow. Actual values of dipping velocity will depend on the properties of the polymer solution.

The position of the lower edge along the base of the polymer valve structure is determined by the depth that the mandrel is inserted into the polymer liquid. If the depth of the insertion of the mandrel into the polymer liquid is controlled within a desired range, the lower edge of the polymer valve structure has a position within desired tolerances without cutting the lower edge of the structure. Generally, the mandrel is dipped at least to a position corresponding to the location at which a sewing cuff is added. However, the mandrel can be dipped to a greater depth. The dip coating can be performed manually by hand or with a mechanical device similar to a drill press to lower the mandrel by the manual rotation/movement of a lever. Alternatively, a motorized linear actuator or robot could be used to lower the mandrel into the solution. Automated dipping provides for greater control of the speed and resolution for more consistency between polymer structures.

Polymer coating from polymer solutions are solidified by evaporating the solvent to leave behind the polymer. The solvent can be removed by exposure of the coated mandrel to the ambient atmosphere or, preferably, in an accelerated process by heating the coated mandrel. The coated mandrel can be heated in an oven or the like. Similarly, polymer melts coated onto a mandrel are solidified by cooling the polymer. Again, the cooling can be performed by exposing the polymer coated mandrel to the ambient atmosphere or under accelerated conditions by further cooling the coated mandrel in a refrigerator or the like.

As noted above, optional reinforcements can be placed within the polymer structure to reinforce the polymer especially near the edge. The reinforcement material can be placed along the mandrel prior to the coating process. Alternatively, the reinforcement material can be placed over a layer of polymer after it is coated onto the mandrel. The reinforcement can be placed over the polymer prior to complete solidification or following solidification. A further polymer layer can be placed on the mandrel following placement of a reinforcing material over a polymer coat.

More than one polymer coating can be applied by dip coating to obtain a thicker polymer structure. Additional layers can be made using the same polymer liquid or a different polymer liquid. In particular, the polymer composition can be the same or different in a plurality of polymer liquids for dip coating. Different polymer compositions can be different with respect to chemical composition, molecular weight differences, concentrations, solvents or other features of the compositions.

Following application of all polymer coats and solidification of the polymer on the mandrel, the polymer structure is separated by removing the polymer along the top of the mandrel. In preferred embodiments with a sharp edge forming a suitable intersection on the top of the mandrel, the polymer on the top of the mandrel can be separated by removing the polymer. The removal, for example, can be performed with tweezers or with vacuum suction. The presence of the sharp edge and a small angle results in a thinning of the polymer along the edge, due to surface tension. Due to the thinning of the polymer at the edge and the presence of the sharp edge, the polymer on the top of the mandrel separates when the polymer is pulled upward. Preferred edges result in separation of the polymer without the application of excessive forces to the polymer that would tear the polymer. The polymer structure can be soaked or otherwise contacted with water or other solvents to facilitate the tearing of the polymer on the top surface.

Separation of the polymer on the top of the mandrel from the remaining polymer forms a polymer valve structure. Then, the polymer valve structure is carefully removed from the mandrel without damaging the polymer. Generally, the polymer is removed from the mandrel manually. The polymer valve structure separated from the mandrel can be processed into a complete prosthesis. If desired, the polymer valve structure can be stored prior to completing the prosthesis, preferably under conditions were the leaflet structures are not damaged.

Formation of Prostheses

After the leaflets are formed, additional processing steps may be needed to complete the production of the prosthesis. In preferred embodiments, the support structure/stent is formed in association with the polymer structure during the dip coating process. In alternative embodiments in which the leaflets were not formed directly in association with a support structure/stent or if an additional support structure is desired, the polymer valve structure is connected to the support structure using, for example, a mechanical fastener, suture or adhesive. Any additional structures, such as a sewing cuff, are connected to the support structure. Sewing cuffs and the like generally are added at or near the inflow edge.

If the valve is incorporated into a conduit, the conduit can be connected to or formed around the valve such that the valve is securely connected to the conduit. Similarly, the valves can be secured within a conduit prior to attaching the conduit to remaining portions of a left ventricular assist device. Suture, staples, adhesive, and other fastening mechanisms and combinations thereof can be used to connect the support structures to the other components.

Packaging, Distribution and Use

For distribution, the medical devices are placed in sealed and sterile containers. The valves can be placed in a holder that supports the base of the valve without damaging the polymer leaflets. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like. Heart valve prostheses and valved vascular prostheses can be implanted, for example, using standard surgical procedures.

Although the present invention has been described with reference to preferred embodiments, workers skilled in the art will recognize that changes may be made in form and detail without departing from the spirit and scope of the invention.

What is claimed is:

1. A mandrel comprising a top surface, and an outer surface comprising a plurality of ridges and contoured surfaces extending between the ridges corresponding to polymer leaflets, wherein an edge on the mandrel separates the top surface and the contoured surfaces, with the mandrel edge corresponding to the free edge of the leaflets, said mandrel edge having a radius of curvature of no more than about 0.25 millimeters.

2. The mandrel of claim 1 wherein the mandrel comprises three ridges connected by three scallops to form three contoured surfaces.

3. The mandrel of claim 1 wherein the mandrel edge has a radius of curvature of no more than about 0.15 millimeters.

4. The mandrel of claim 1 wherein the angle between the top surface and the contoured surfaces is no larger than about 135 degrees.

5. The mandrel of claim 1 wherein the angle between the top surface and the contoured surfaces is no larger than about 90 degrees.

6. The mandrel of claim 1 wherein the top surface of the mandrel is flat.

7. The mandrel of claim 1 wherein the top surface of the mandrel has flat portions and curved portions.

8. The mandrel of claim 1 wherein the top surface of the mandrel has flat portions adjacent the edge and a protruding portion away from the edge.

9. The mandrel of claim 1 wherein the contoured surfaces are on an outside surface of the mandrel.

10. The mandrel of claim 1 wherein the contoured surfaces are on an interior surface of the mandrel.

11. A mandrel comprising an outer surface having a plurality of ridges and contoured surfaces extending between the ridges corresponding to polymer leaflets in a closed configuration, wherein contoured surfaces corresponding to the leaflets meet contoured surfaces of adjacent leaflets at an edge, said edge having a radius of curvature of no more than about 0.25 millimeters.

12. The mandrel of claim 1 wherein the top surface of the mandrel is convex.

13. The mandrel of claim 1 wherein the top surface of the mandrel is concave.

14. The mandrel of claim 1 comprising a groove parallel to the edge of the top surface.

15. The mandrel of claim 14 wherein the groove has a depth from about 0.01 millimeter to about 1 millimeter.

16. The mandrel of claim 1 wherein the mandrel edge has a radius of curvature of no more than about 0.1 millimeter.

17. The mandrel of claim 1 comprising a polymer on the contoured surfaces.

18. The mandrel of claim 11 comprising a polymer on the contoured surfaces.

19. A mandrel for forming leaflets of valved prostheses, the mandrel comprising:

an end surface; and a sidewall surface comprising a contoured surface section conformal with a shape of a leaflet, the leaflet having a free edge, the contoured surface section having a curvature which varies and at least a portion of which curves outwardly relative to the mandrel;

wherein the contoured surface section and at least an adjacent region of the end surface have a predetermined wetting property for receiving a polymer composition having a predetermined viscosity; and wherein the contoured surface section intersects the end surface to form a boundary that corresponds to the free edge of the leaflet, the boundary generally having a radius of curvature.

20. The mandrel of claim 19 wherein the contoured surface section intersects the end surface generally at no more than about a 135 degree angle and generally with the radius of curvature being no more than about 0.25 mm.

21. The mandrel of claim 19 wherein the contoured surface section intersects the end surface generally at no more than about a 90 degree angle and generally with the radius of curvature being no more than about 0.1 mm.

22. The mandrel of claim 19 wherein the contoured surface section intersects the end surface generally at no more than about a 135 degree angle.

23. The mandrel of claim 19 wherein the contoured surface section intersects the end surface generally at no more than about a 105 degree angle.

24. The mandrel of claim 19 wherein the contoured surface section intersects the end surface generally at no more than about a 90 degree angle.

25. The mandrel of claim 19 wherein the radius of curvature is no more than about 0.25 mm.

26. The mandrel of claim 19 wherein the radius of curvature is no more than about 0.15 mm.

27. The mandrel of claim 19 wherein the radius of curvature is no more than about 0.1 mm.

28. The mandrel of claim 19 wherein the mandrel is a male mandrel.

29. The mandrel of claim 19 wherein the mandrel is a female mandrel.

30. The mandrel of claim 19 wherein the contoured surface section comprises a groove parallel to the boundary.

31. The mandrel of claim 19 wherein:

the sidewall surface further comprises an additional surface section conformal with the shape of the leaflet in a relaxed state;

the additional contoured surface section has the predetermined wetting property; and the additional contoured surface section intersects the end surface to form an additional boundary that corresponds to the free edge of the leaflet, the additional boundary generally having a radius of curvature comparable to the predetermined polymer coating thickness.

32. The mandrel of claim 19 wherein the contoured surface section includes at least a portion which curves inwardly relative to the mandrel.

* * * * *